United States Patent [19]

Ohdan et al.

[11] 4,444,907
[45] Apr. 24, 1984

[54] METHACRYLIC ACID PRODUCTION CATALYST

[75] Inventors: Kyoji Ohdan; Toshihiko Hogami; Masataka Fujinaga, all of Ube, Japan

[73] Assignee: Ube Industries, Ltd., Yamaguchi, Japan

[21] Appl. No.: 448,059

[22] Filed: Dec. 9, 1982

[30] Foreign Application Priority Data

Dec. 24, 1981 [JP] Japan ................... 56-208110

[51] Int. Cl.$^3$ ............................................. B01J 27/14
[52] U.S. Cl. .................................... 502/211; 502/209; 502/210; 502/212
[58] Field of Search ................ 252/437, 435; 502/209, 502/210, 211, 212

[56] References Cited

U.S. PATENT DOCUMENTS

| | | | |
|---|---|---|---|
| 3,379,652 | 4/1968 | Young | 252/435 X |
| 3,998,876 | 12/1976 | Koto et al. | 252/437 X |
| 4,072,708 | 2/1978 | White et al. | 252/437 X |
| 4,075,123 | 2/1978 | White et al. | 252/437 |
| 4,075,124 | 2/1978 | White et al. | 252/435 X |
| 4,110,369 | 8/1978 | White et al. | 252/437 X |
| 4,139,719 | 2/1979 | White et al. | 252/435 X |
| 4,283,288 | 8/1981 | Udovich et al. | 502/209 |
| 4,314,074 | 2/1982 | Khoobiar | 252/437 X |
| 4,333,853 | 6/1982 | Milberger et al. | 502/209 |

*Primary Examiner*—William G. Wright
*Attorney, Agent, or Firm*—Burgess, Ryan & Wayne

[57] ABSTRACT

A heteropolyacid type catalyst capable of producing methacrylic acid from methacrolein and molecular oxygen at an extremely high yield for a long time at a relatively low temperature for a short contacting time under a vapor phase is provided. This catalyst is prepared by:

(a) mixing molybdophosphoric acid and compounds containing the other constituent elements of the catalyst with each other in the presence of water;
(b) concentrating or drying the resultant solution or slurry;
(c) adjusting the water content of the resultant concentrated or dried mixture to 5% to 20% by weight; and
(d) heat treating the mixture at a temperature of 100° C. to 300° C.

5 Claims, No Drawings

METHACRYLIC ACID PRODUCTION CATALYST

BACKGROUND OF THE INVENTION

1. Field of the Invention

The present invention relates to a heteropolyacid type catalyst containing, as catalyst constituent elements, phosphorus, molybdenum, copper and arsenic and suitable for use in the production of methacrylic acid, at a high yield, from methacrolein and molecular oxygen at an elevated temperature under a vapor phase.

2. Description of the Prior Art

It is known in the art that methacrylic acid is produced by the vapor phase reaction of methacrolein and molecular oxygen in the presence of heteropolyacid type catalysts containing as catalyst constituent elements, phosphorus, molybdenum, copper and arsenic, at an elevated temperature. The known heteropolyacid type catalysts are generally prepared by first mixing suitable compounds containing the constituent elements of the catalysts, for example, oxides and phosphates and, optionally, suitable supports, in the presence of, for example, water; drying, generally evaporating to dryness, the resultant mixture in the form of a solution or slurry; and optionally calcining the dried mixture, with or without molding the dried mixture, as disclosed in, for example, U.S. Pat. Nos. 3,998,876, 4,075,123, 4,075,124 and 4,110,369.

Heteropolyacids or their salts containing phosphorus and molybdenum are believed to form a so-called Keggin structure as a skelton structure, which structure is surrounded by protons, or cations, and water of crystallization. Zero to 30 molecules of water of crystallization per molecule of the heteropolyacids is included in the heteropolyacids.

SUMMARY OF THE INVENTION

The object of the present invention is to provide a new heteropolyacid type catalyst containing, as catalyst constituent elements, phosphorus, molybdenum, copper, and arsenic, which is capable of producing methacrylic acid from methacrolein and molecular oxygen at an elevated temperature under a vapor phase at a yield higher than that of conventional heteropolyacid type catalysts.

Other objects and advantages of the present invention will be apparent from the following description.

In accordance with the present invention, there is provided a method for preparing a heteropolyacid type catalyst containing, as catalyst constituent elements, phosphorus, molybdenum, copper and arsenic and suitable for use in the production of methacrylic acid from methacrolein and molecular oxygen at an elevated temperature under a vapor phase comprising the steps of:

(a) mixing molybdophosphoric acid and compounds containing the other constituent elements of the catalyst in the presence of water;

(b) concentrating or drying the resultant solution or slurry;

(c) adjusting the water content of the resultant concentrated or dried mixture to 5% to 20% by weight; and (d) heat treating the mixture at a temperature of 100° C. to 300° C.

DESCRIPTION OF THE PREFERRED EMBODIMENTS

According to the present invention, heteropolyacid type catalysts containing, as essential catalyst constituent elements, phosphorus, molybdenum, copper, and arsenic, and suitable for use in the production of methacrylic acid can be effectively prepared. In addition to the above-mentioned four essential catalyst constituent elements (i.e., phosphorus, molybdenum, copper and arsenic), heteropolyacid type catalysts which can be produced according to the present invention can contain catalyst constituent elements used in the conventional these type catalysts. Examples of such elements are tungsten, iron, bismuth, antimony, cobalt, zinc, zirconium, calcium, chromium, boron, tin, titanium, palladium, tantalum, cerium, vanadium, magnesium, silver, aluminum, and potassium.

The present invention can be applied to prepare a catalyst for producing methacrylic acid having the following general composition formula:

$$Mo_{12}P_aCu_bAs_cX_dO_e$$

wherein Mo is molybdenum, P is phosphorus, Cu is copper, As is arsenic, X is at least one metal selected from the group consisting of tungsten, iron, bismuth, antimony, cobalt, zinc, boron, chromium, zirconium, vanadium, titanium and tin, and O is oxygen, and the subscripts a, b, c, d and e are the number of atoms, where when the number of Mo is 12, a=0.9 to 2, desirably 1 to 1.6, b=0.005 to 3, desirably 0.01 to 1, c=0.01 to 2, desirably 0.1 to 1.5, d=0 to 2, desirably 0.001 to 1 and e is the number determined by the valance of each atom. Thus, catalysts capable of producing methacrylic acid from methacrolein at an extremely high yield for a long time at a relatively low temperature for a short contacting time can be prepared.

In the practice of the present invention, molybdophosphoric acid should be used as the molybdenum source. If molybdenum containing compounds, other than molybdophosphoric acid, such as ammonium molybdate are used, catalysts having satisfactory selectivity to methacrylic acid cannot be obtained due to the formation of ammonium salts of heteropolyacids. Furthermore, if molybdenum oxide and molybdic acid are used, a long time is required to form a stable molybdophosphoric acid compound and the preparation of a catalyst having a satisfactory catalyst performance is difficult.

The molybdophosphoric acids usable as the molybdenum source in the present invention are not only those having an atomic ratio of P/Mo of 1/12, but also any known molybdophosphoric acids having atomic ratios of P/Mo of, for example, 1/11, 1/10, 1/9 and 2/17.

In the practice of the present invention, the heteropolyacid type catalysts are generally prepared in the following manner. Molybdophosphoric acid and compounds containing the other constituent elements of the catalyst are first mixed with each other in the presence of water to form an aqueous solution or slurry. Typical examples of the compounds containing the other constituent elements of the catalyst are: phosphor compounds such as phosphoric acid and phosphorus oxides; copper compounds such as copper oxides, copper nitrates and copper carbonates; arsenic compounds such as arsenic acid, arsenic oxide; and oxides, hydroxides and carbonate of the other elements such as tungsten, iron, bismuth, antimony, cobalt, zinc, zirconium, calcium, chromium, boron, tin, titanium, palladium, tantalum, cerium, vanadium, magnesium, silver, aluminum and potassium, and the like.

The order of the mixing of the molybdophosphoric acid and compounds containing the other constituent elements of the catalyst in the presence of water is not specially limited, but it is desirable that the molybdophosphoric acid be first dissolved in water and that then the compounds containing the other constituent elements of the catalyst be mixed therewith.

According to the present invention, it is desirable, after the mixing, that the aqueous solution or slurry be aged at a temperature of 20° C. to 100° C., desirably 30° C. to 80° C., for at least 3 hours, desirably 5 to 30 hours, while stirring. The aging allows the resultant catalyst to exhibit a higher yield of methacrylic acid. The mechanism of the increase in the methacrylic acid yield due to the aging is not clearly understood, but it would seem that, without prejudice to the present invention, the aging modifies the crystal structure of the heteropolyacid of molybdophosphoric acid, thereby forming new heteropolyacid containing the other constituent elements of the catalyst.

Furthermore, when organic reducing substances including: oxycarboxylic acids such as glycolic acid, glyoxylic acid and lactic acid; glycols such as ethylene glycol, propylene glycol, and polyalkylene glycol; and sugars such as dextrin, starch, aldose, and lactose are added to the above-mentioned mixed solution or slurry, the reproducibility of the catalyst is improved and the catalytic performance is also improved. The amount of the organic reducing substances is suitably 0.3% to 12% by weight, desirably 0.5% to 9% by weight, based on the weight of the resultant catalyst, although the amount depends upon the types of the organic reducing substances used. The yield of methacrylic acid is decreased when the amount of the organic reducing substances used is either too large or too small. There is no significant difference in the catalytic performance of the catalyst, when the organic reducing substances are used alone or in any mixture thereof.

According to the present invention, molybdophosphoric acid and compounds containing the other constituent elements of the catalyst are mixed with each other in the presence of water and, then, the resultant aqueous solution or slurry is concentrated or dried. The water content of the resultant concentrated or dried mixture is, then, adjusted to 5% to 20% by weight, desirably 7% to 18% by weight. This adjustment can be conveniently carried out as follows. For instance, the aqueous solution or slurry is concentrated in, for example, a rotary evaporator until the desired water content in the concentrated mixture can be obtained. Alternatively, the aqueous solution or slurry is dried by means of, for example, an evaporation to dryness method or spray drying method and, then, the water content of the dried mixture is adjusted to the desired value by the addition of water.

The concentrated or dried mixture, the water content of which has been previously adjusted to the desired value, is subjected to a thermal or heat treatment, with or without molding, at a temperature of 100° C. to 300° C., desirably 130° C. to 250° C.

In the practice of the present invention, the adjustment of the water content and the thermal or heat treatment temperature are very important.

If the water content is not adjusted within the above-mentioned range, a catalyst exhibiting a high methacrylic acid yield cannot be obtained. Further a too large or too small water content results in poor moldability during the molding of the dried mixture. Even if the water content of the concentrated or dried mixture is adjusted within the above-mentioned range, a catalyst exhibiting a high methacrylic acid yield cannot be obtained if the thermal or heat treatment temperature is too high or too low.

In the practice of the present invention, the thermal or heat treatment should be carried out within the above-mentioned temperature range. However, it is desirable that, in order to effect the thermal or heat treatment effectively, the concentrated or dried mixture, the water content of which has been previously adjusted within the above-mentioned range, be first subjected to rapid thermal or heat treatment in a heating vessel previously heated to a temperature of 100° C. to 300° C. to effect the dehydration of the concentrated or dried mixture. The thermal or heat treatment is generally carried out for at least 1 hour, desirably 1 to 20 hours, suitably in, for example, oxygen-containing gas (e.g., air). Thus, according to the present invention, a desired catalyst, which exhibits a higher methacrylic acid yield than that of the conventional catalyst containing phosphorus, molybdenum, copper and arsenic, can be obtained by adjustment of the water content and subsequent thermal or heat treatment, desirably rapid thermal or heat treatment. The reasons of the improvement in the methacrylic acid yield of the present catalyst is not clearly understood, but it would seem that, without prejudice to the present invention, the adjustment of the water content and the thermal or heat treatment as well as the previously mentioned optional aging and use of the organic reducing substance cause a change or modification in the crystal structure of the resultant heteropolyacid, thereby increasing the catalyst activity.

The catalyst constituent elements of the catalyst obtained by the present invention are present in the form of a mixture of heteropolyacids such as molybdophosphoric acid and copper salts thereof, as well as the composite oxides, in which plural catalyst constituent elements are bonded with oxygen, and the oxide of each catalyst constituent element alone.

In the practice of the present invention, the desired catalyst may be prepared by the addition of a support during the preparation of the catalyst. Furthermore, when the catalyst according to the present invention is used in the production of the catalyst, a support may be used together with the catalyst.

The supports usable in the practice of the present invention are any supports which are conventionally used in catalysts for use in the production of, for example, acrylic acid and methacrylic acid. Examples of such supports are diatomaceous earth, alumina, silica, silica sol, silicon carbide, and graphite.

When methacrolein is reacted with molecular oxygen to produce methacrylic acid in a vapor phase at an elevated reaction temperature in the presence of the catalyst prepared according to the present invention, pure oxygen gas can, of course, be used. However, since a high purity of oxygen is not required in this process, air is conveniently used from an economical point of view. Furthermore, when the above-mentioned reaction is carried out, a gaseous diluent may be advantageously used together with the molecular oxygen and the methacrolein. The gaseous diluents usable in the practice of the above-mentioned reaction are those which do not adversely affect the reaction. Examples of such diluents are gaseous nitrogen, carbon dioxide, and steam. Among these diluents, the use of steam is advantageous because steam not only improves the conversion of methacrolein and the selectivity to methacrylic acid, but also prolongs the life of the catalytic activity.

It is not necessary to use, as a starting material, methacrolein having a high purity as in the molecular oxygen. For example, methacrolein obtained from the oxidation reaction of isobutylene can be used in the above-mentioned reaction.

The production reaction of methacrylic acid according to the present invention can be carried out in any known reaction vessel including a fluidized bed reactor, a moving bed reactor, and a fixed bed reactor. Since the catalysts prepared according to the present invention have the advantages in that a high conversion of methacrolein and a high selectivity to methacrylic acid can be obtained at a relatively low reaction temperature and a short contact time and that the catalyst activity is prolonged for a long period of time, the fixed bed reactor is advantageously used in the practice of the production of methacrylic acid.

The production process of methacrylic acid can be carried out under normal pressure, elevated pressure or reduced pressure, but, in general, normal pressure can be conveniently used. The reaction temperature is desirably within the range of 200° C. to 400° C. more desirably, 250° C. to 350° C., most desirably, 260° C. to 350° C. The contact time is within the range of 0.1 to 10 seconds, desirably, 0.5 to 5 seconds. In the practice of the reaction, a mixed gas containing methacrolein, molecular oxygen, generally air, and steam is desirably used. Although the composition of the mixed gas to be used may be varied over a wide range, typical examples of the composition of the mixed gas are 0.5 to 7 moles, desirably 1 to 5 moles, of molecular oxygen, and 0.5 to 30 moles, desirably 1 to 10 moles, of steam, based on 1 mol of methacrolein. The methacrylic acid thus produced can be recovered according to any of the conventional techniques such as condensation and solvent extraction.

EXAMPLE

The present invention now will be further illustrated by, but is by no means limited to, the following Examples together with Comparative Examples.

In the Examples and the Comparative Examples, the conversion (%), the selectivity (%) and the yield (%) are determined by the following equations.

$$\text{Conversion (\%)} = \frac{\text{Moles of methacrolein reacted}}{\text{Moles of methacrolein fed}} \times 100$$

$$\text{Selectivity (\%)} = \frac{\text{Moles of methacrylic acid produced}}{\text{Moles of methacrolein reacted}} \times 100$$

$$\text{Yield (\%)} = \frac{\text{Moles of methacrylic acid produced}}{\text{Moles of methacrolein fed}} \times 100$$

EXAMPLE 1

(Preparation of Catalyst)

One hundred grams of molybdophosphoric acid ($H_3P_1Mo_{12}O_{40}.29H_2O$) was dissolved in about 300 ml of water at about 25° C. Then, to this solution, 0.34 g of cupric oxide (CuO) and 6.0 g of a 60% aqueous solution of arsenic acid ($H_3AsO_4$) were added and mixed with each other. Therefore, 1 g of ethylene glycol was added thereto and, then, the mixture was aged at a temperature of 50° C. for 20 hours while stirring.

The mixed solution obtained above was concentrated under vacuum in a rotary evaporator until the water content thereof became 15%. The concentrated mixture having a water content of 15% was placed in a heating vessel, the temperature in which was maintained to 150° C. Thus, the concentrated mixture was subjected to a thermal or heat treatment for 18 hours in an air environment. Thereafter, 1% of graphite was added to the resultant mixture and, then, the mixture was molded to a catalyst in the form of pellets each having a size of 4 mm$\phi$ × 4 mmH. The catalyst thus obtained had a atomic ratio of Mo:P:Cu:As = 12:1:0.1:0.6.

(Production of Methacrylic Acid)

9.3 ml (13.1 g) amount of the catalyst obtained above was packed into a U-shaped glass reaction tube having an inner diameter of 8 mm$\phi$. A mixed gas containing 4% by volume of methacrolein, 10% by volume of oxygen, 30% by volume of steam, and 56% by volume of nitrogen was then fed to the reactor, at a flow rate of 400 ml/min, and was catalytically reacted at a temperature of 290° C. for 1 hour. The contact time was 1.4 seconds.

The results of the catalytic reaction are shown in Table 1.

Comparative Example 1

A catalyst was prepared in the same manner as in Example 1, except that the water content of the concentrated mixture was not adjusted and the mixture was evaporated to dryness in the evaporator.

The catalytic reaction was carried out by using the catalyst obtained above in the same manner as in Example 1. The results are shown in Table 1.

Comparative Example 2

A catalyst was prepared in the same manner as in Example 1, except that 91 g of ammonium molybdate [$(NH_4)_6Mo_7O_{24}.4H_2O$] and 4.9 of 85% phosphoric acid ($H_3PO_4$) were used in lieu of the molybdophosphoric acid.

The catalytic reaction was carried out by using the catalyst obtained above in the same manner as in Example 1. The results are shown in Table 1.

TABLE 1

| No. | Conversion of methacrolein (%) | Selectivity to methacrylic acid (%) | Yield of methacrylic acid (%) |
| --- | --- | --- | --- |
| Example 1 | 97.7 | 87.6 | 85.7 |
| Comparative Example 1 | 93.0 | 85.6 | 79.6 |
| Comparative Example 2 | 94.1 | 80.5 | 75.8 |

EXAMPLE 2

(Preparation of Catalyst)

One hundred grams of molybdophosphoric acid ($H_3P_1Mo_{12}O_{40}.29H_2O$) was dissolved in about 300 ml of water at about 25° C. Then, to this solution, 0.68 g of cupric oxide (CuO), 6.0 g of a 60% aqueous solution of arsenic acid ($H_3AsO_4$) and 0.62 g of antimony trioxide ($Sb_2O_3$) were added and mixed with each other. Thereafter, 2 g of ethylene glycol was added thereto and, then, the mixture was aged at a temperature of 50° C. for 20 hours while stirring.

The mixed solution obtained above was concentrated under vacuum in a rotary evaporator until the water content thereof became 10%. The concentrated mixture having a water content of 10% was allowed to stand for 24 hours at room temperature. No substantial change in the water content of the concentrated mixture was observed. The concentrated mixture was then subjected to a thermal or heat treatment at a temperature of 130° C. for 10 hours. Thereafter, 1% of graphite was added to the resultant mixture and, then, the mixture was molded to a catalyst in the form of pellets each having a size of 4 mm$\phi$×4 mmH. The catalyst thus obtained had a atomic ratio of Mo:P:Cu:As:Sb=12:1:0.2:0.6:0.1.

(Production of Methacrylic Acid)

The catalytic reaction of Example 1 was carried out by using the above-prepared catalyst. The results of the catalytic reaction are shown in Table 2.

EXAMPLES 3 TO 13

Catalysts were prepared in the same manner as described in Example 2, except that the atomic ratios of the catalyst constituent elements were changed as shown in Table 2. The starting materials used for the preparation of the catalysts, other than those mentioned in Example 2, were bismuth oxide ($Bi_2O_3$) as a bismuth source, tungsten oxide ($WO_3$) as a tungsten source, chromium oxide ($Cr_2O_3$) as a chromium source, boric acid ($H_3BO_3$) as a boron source and ferric oxide ($Fe_2O_3$) as a ferric source. In the preparation of the catalysts having an atomic ratio of P of more than 1, phosphoric acid was additionally used.

The catalytic reactions were carried out by using the catalysts obtained above in the same reaction conditions as used in Example 1. The results of the catalytic reactions are shown in Table 2.

treatment temperature was changed from 130° C. to 350° C.

The catalytic reaction was carried out by using the above-prepared catalyst in the same reaction conditions as in Example 1. The results are shown in Table 3.

EXAMPLE 14

A catalyst was prepared in the same manner as described in Example 2, except that the aging conditions was changed from 50° C.×20 hours to 60° C.×15 hours.

The catalytic reaction was carried out by using the above-prepared catalyst in the same reaction conditions as in Example 1. The results are shown in Table 3.

EXAMPLE 15

A catalyst was prepared in the same manner as described in Example 2, except that the water content of the concentrated mixture was changed from 10% to 18%.

The catalytic reaction was carried out by using the above-prepared catalyst in the same reaction conditions as in Example 1. The results are shown in Table 3.

EXAMPLE 16

A catalyst was prepared in the same manner as described in Example 2, except that the thermal or heat treatment temperature was changed from 130° C. to 180° C.

The catalytic reaction was carried out by using the above-prepared catalyst in the same reaction conditions as in Example 1. The results are shown in Table 3.

TABLE 2

| Example No. | Catalyst constituent element (atomic ratio) | | | | | Conversion of methacrolein (%) | Selectivity to methacrylic acid (%) | Yield of methacrylic acid (%) |
| --- | --- | --- | --- | --- | --- | --- | --- | --- |
| | Mo | P | Cu | As | X | | | |
| 2 | 12 | 1 | 0.2 | 0.6 | Sb = 0.1 | 97.3 | 87.4 | 85.0 |
| 3 | 12 | 1 | 0.05 | 0.5 | 0 | 96.9 | 87.1 | 84.4 |
| 4 | 12 | 1.1 | 0.1 | 0.5 | 0 | 96.5 | 87.3 | 84.2 |
| 5 | 12 | 1 | 0.1 | 0.7 | Sb = 0.1 | 97.2 | 86.9 | 84.5 |
| 6 | 12 | 1.2 | 0.3 | 0.4 | Sb = 0.1 W = 0.05 | 97.5 | 87.5 | 85.3 |
| 7 | 12 | 1 | 0.4 | 0.8 | 0 | 96.5 | 86.9 | 83.9 |
| 8 | 12 | 1 | 0.1 | 0.6 | Cr = 0.1 | 97.3 | 88.0 | 85.6 |
| 9 | 12 | 1 | 0.1 | 0.6 | Fe = 0.1 | 97.5 | 87.9 | 85.7 |
| 10 | 12 | 1 | 0.1 | 0.6 | B = 0.1 | 96.9 | 88.2 | 85.5 |
| 11 | 12 | 1.05 | 0.5 | 0.4 | Bi = 0.1 Cr = 0.1 | 96.9 | 88.3 | 85.6 |
| 12 | 12 | 1 | 0.15 | 0.55 | 0 | 96.4 | 86.9 | 83.8 |
| 13 | 12 | 1 | 0.1 | 0.5 | Sb =0.1 W = 0.1 | 97.8 | 87.9 | 85.9 |

Comparative Example 3

A catalyst was prepared in the same manner as described in Example 2, except that the water content of the concentrated mixture was changed from 10% to 1%.

The catalytic reaction was carried out by using the above-prepared catalyst in the same reaction conditions as in Example 1. The results are shown in Table 3.

Comparative Example 4

A catalyst was prepared in the same manner as described in Example 2, except that the thermal or heat

TABLE 3

| No. | Conversion of methacrolein (%) | Selectivity to methacrylic acid (%) | Yield of methacrylic acid (%) |
| --- | --- | --- | --- |
| Comparative Example 3 | 95.2 | 84.6 | 80.5 |
| Comparative Example 4 | 94.7 | 85.0 | 80.5 |
| Example 14 | 97.2 | 87.8 | 85.3 |
| Example 15 | 96.4 | 87.4 | 84.2 |
| Example 16 | 97.0 | 88.1 | 85.5 |

We claim:
1. A method for preparing a heteropolyacid type catalyst containing, as catalyst constituent elements, phosphorus, molybdenum, copper, and arsenic and suitable for use in the production of methacrylic acid from methacrolein and molecular oxygen at an elevated temperature under a vapor phase, comprising the steps of:
(a) mixing molybdophosphoric acid and compounds containing the other constituent elements of the catalyst in the presence of water;
(b) concentrating or drying the resultant solution or slurry;
(c) adjusting the water content of the resultant concentrated or dried mixture to 5% to 20% by weight; and
(d) heat treating the mixture at a temperature of 100° C. to 300° C.

2. A method as claimed in claim 1, wherein the catalyst has the general composition formula $$Mo_{12}P_aCu_bAs_cX_dO_e$$

wherein Mo is molybdenum, P is phosphorus, Cu is copper, As is arsenic, X is at least one metal selected from the group consisting of tungsten, iron, bismuth, antimony, cobalt, zinc, boron, chromium, zirconium, vanadium, titanium and tin, and O is oxygen; and the subscripts a, b, c, d and e are the number of atoms, where when the number of Mo is 12, a=0.9 to 2, b=0.005 to 3, c=0.01 to 2, d=0 to 2, and e is the number determined by the valance of each atom.

3. A method as claimed in claim 1, wherein the aqueous mixture obtained in step (a) is aged at a temperature of 20° C. to 100° C. for at least 3 hours while stirring.

4. A method as claimed in claim 1, wherein at least one organic reducing agent selected from the group consisting of oxycarboxylic acids, glycols, and sugars is added to the aqueous mixture obtained in step (a).

5. A heteropolyacid type catalyst containing, as catalyst constituent elements, phosphorus, molybdenum, copper, and arsenic and suitable for use in the production of methacrylic acid from methacrolein and molecular oxygen at an elevated temperature under a vapor phase, prepared by the steps of:
(a) mixing molybdophosphoric acid and compounds containing the other constituent elements of the catalyst with each other in the presence of water;
(b) concentrating or drying the resultant solution or slurry;
(c) adjusting the water content of the resultant concentrated or dried mixture to 5% to 20% by weight; and
(d) heat treating the mixture at a temperature of 100° C. to 300° C.

* * * * *